United States Patent
Larson et al.

(10) Patent No.: US 8,142,354 B1
(45) Date of Patent: Mar. 27, 2012

(54) LAMINATED SURGICAL ACCESS PORT

(75) Inventors: Kevin A. Larson, South Lebanon, OH (US); Victor C. Moreno, Terrace Park, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 986 days.

(21) Appl. No.: 11/928,118

(22) Filed: Oct. 30, 2007

(51) Int. Cl.
*A61B 1/32* (2006.01)
(52) U.S. Cl. .................................. 600/203; 600/246
(58) Field of Classification Search .............. 600/203, 600/206, 208, 233
See application file for complete search history.

(56) References Cited

U.S. PATENT DOCUMENTS

| | | | |
|---|---|---|---|
| 1,157,202 A | 10/1915 | Bates et al. | |
| 4,889,107 A * | 12/1989 | Kaufman | 600/206 |
| 5,326,363 A | 7/1994 | Aikins | |
| 5,470,354 A | 11/1995 | Hershberger et al. | |
| 5,480,410 A | 1/1996 | Cuschieri et al. | |
| 5,514,133 A | 5/1996 | Golub et al. | |
| 5,524,644 A | 6/1996 | Crook | |
| 5,640,977 A | 6/1997 | Leahy et al. | |
| 5,649,550 A | 7/1997 | Crook | |
| 5,656,785 A | 8/1997 | Trainor et al. | |
| 5,752,965 A | 5/1998 | Francis et al. | |
| 5,813,409 A | 9/1998 | Leahy et al. | |
| 5,853,395 A | 12/1998 | Crook et al. | |
| 5,906,577 A | 5/1999 | Beane et al. | |
| 6,033,426 A | 3/2000 | Kaji | |
| 6,086,570 A * | 7/2000 | Aboul-Hosn et al. | 604/256 |
| 6,142,936 A | 11/2000 | Beane et al. | |
| 6,254,533 B1 | 7/2001 | Fadem et al. | |
| 6,254,534 B1 | 7/2001 | Butler et al. | |
| 6,440,063 B1 | 8/2002 | Beane et al. | |
| 6,450,983 B1 | 9/2002 | Rambo | |
| 6,578,577 B2 | 6/2003 | Bonadio et al. | |
| 6,582,364 B2 | 6/2003 | Butler | |
| 6,589,211 B1 | 7/2003 | MacLeod | |
| 6,846,287 B2 | 1/2005 | Bonadio et al. | |
| 6,887,194 B2 | 5/2005 | Hart et al. | |
| 6,908,430 B2 | 6/2005 | Caldwell et al. | |
| 6,958,037 B2 | 10/2005 | Ewers et al. | |
| 7,473,221 B2 * | 1/2009 | Ewers et al. | 600/208 |
| 7,727,146 B2 * | 6/2010 | Albrecht et al. | 600/208 |
| 7,736,306 B2 * | 6/2010 | Brustad et al. | 600/208 |
| 7,766,824 B2 * | 8/2010 | Jensen et al. | 600/208 |
| 2001/0037053 A1 | 11/2001 | Bonadio et al. | |
| 2002/0010389 A1 | 1/2002 | Butler et al. | |
| 2002/0068923 A1 | 6/2002 | Caldwell et al. | |

(Continued)

FOREIGN PATENT DOCUMENTS

EP 1135070 9/2004

(Continued)

OTHER PUBLICATIONS

Co-owned and co-pending U.S. Appl. No. 11/928,118.

(Continued)

*Primary Examiner* — Nicholas Woodall

(57) ABSTRACT

A surgical access port comprises a wound protector adapted for insertion into a wound in the abdominal wall of a patient. A resilient pad comprising a laminated structure with a plurality of layers of resilient materials is attached to the wound protector. The pad comprises an aperture adapted to receive and seal against a surgeon's arm or surgical instruments and is self-closing in the absence of a surgeon's arm or surgical instrument.

5 Claims, 6 Drawing Sheets

U.S. PATENT DOCUMENTS

| | | | |
|---|---|---|---|
| 2002/0097793 | A1 | 7/2002 | Struhsaker et al. |
| 2002/0183594 | A1 | 12/2002 | Beane et al. |
| 2004/0015185 | A1 | 1/2004 | Ewers et al. |
| 2004/0049099 | A1 | 3/2004 | Ewers et al. |
| 2004/0092795 | A1 | 5/2004 | Bonadio et al. |
| 2004/0097793 | A1 | 5/2004 | Butler et al. |
| 2004/0127772 | A1 | 7/2004 | Ewers et al. |
| 2004/0154624 | A1 | 8/2004 | Bonadio et al. |
| 2004/0254426 | A1 | 12/2004 | Wenchell |
| 2004/0267096 | A1 | 12/2004 | Caldwell et al. |
| 2005/0020884 | A1 | 1/2005 | Hart et al. |
| 2005/0059865 | A1 | 3/2005 | Kahle et al. |
| 2005/0090716 | A1 | 4/2005 | Bonadio et al. |
| 2005/0222582 | A1 | 10/2005 | Wenchell |
| 2005/0241647 | A1 | 11/2005 | Nguyen et al. |
| 2005/0288558 | A1 | 12/2005 | Ewers et al. |
| 2006/0084842 | A1 | 4/2006 | Hart et al. |
| 2006/0229501 | A1* | 10/2006 | Jensen et al. .................. 600/235 |
| 2006/0247500 | A1 | 11/2006 | Voegele et al. |
| 2007/0088202 | A1 | 4/2007 | Albrecht et al. |
| 2007/0088204 | A1 | 4/2007 | Albrecht et al. |
| 2007/0149859 | A1 | 6/2007 | Albrecht et al. |
| 2007/0239165 | A1 | 10/2007 | Amirouche |
| 2008/0021362 | A1 | 1/2008 | Fihe et al. |
| 2008/0281161 | A1 | 11/2008 | Albrecht et al. |
| 2009/0082631 | A1 | 3/2009 | Cronin et al. |
| 2009/0137879 | A1* | 5/2009 | Ewers et al. .................. 600/208 |
| 2010/0249527 | A1* | 9/2010 | Brustad et al. ................ 600/208 |

FOREIGN PATENT DOCUMENTS

| | | |
|---|---|---|
| EP | 1312318 | 12/2005 |
| EP | 1707159 | 11/2008 |
| EP | 1402857 | 8/2010 |
| WO | WO 9524864 | 9/1995 |
| WO | WO 9848724 | 11/1998 |
| WO | WO 0032116 | 6/2000 |
| WO | WO 0054676 | 9/2000 |
| WO | WO 0054677 | 9/2000 |
| WO | WO 0126558 | 4/2001 |
| WO | WO 0234108 | 5/2002 |
| WO | WO 2004030547 | 4/2004 |
| WO | WO 2004054456 | 7/2004 |
| WO | WO 2004096012 | 11/2004 |
| WO | WO 2005097019 | 10/2005 |
| WO | WO 2005097234 | 10/2005 |
| WO | WO 2010022272 | 2/2010 |

OTHER PUBLICATIONS

Co-owned and co-pending U.S. Appl. No. 11/928,156.
Co-owned and co-pending U.S. Appl. No. 11/928,177.
Co-owned and co-pending U.S. Appl. No. 11/928,192.
Co-owned and co-pending U.S. Appl. No. 11/928,215.
Co-owned and co-pending U.S. Appl. No. 11/928,228.
Co-owned and co-pending U.S. Appl. No. 12/192,205.
International Search Report Dated Jun. 15, 2010, International Application No. 10156105.8-2319.

* cited by examiner

LAMINATED SURGICAL ACCESS PORT

BACKGROUND

The present invention relates in general to surgical devices and procedures, and more particularly to access devices.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic and arthroscopic procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have a sealing valve that prevent the insufflatory fluid from escaping while an instrument is positioned in the trocar. As a further example, hand access ports are also used during endoscopic surgery, sometimes referred to as hand assisted laparoscopic surgery ("HALS"). A hand access port will typically seal around a surgeon's hand or arm to prevent the insufflatory fluid from escaping while allowing the surgeon to manipulate tissue within the patient's body. Iris valves, gel pads, and inflatable balloons are some examples of seals used in HALS access ports.

While surgical access devices are known, no one has previously made or used a surgical access device in accordance with the present invention.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

DETAILED DESCRIPTION

Figure 1:
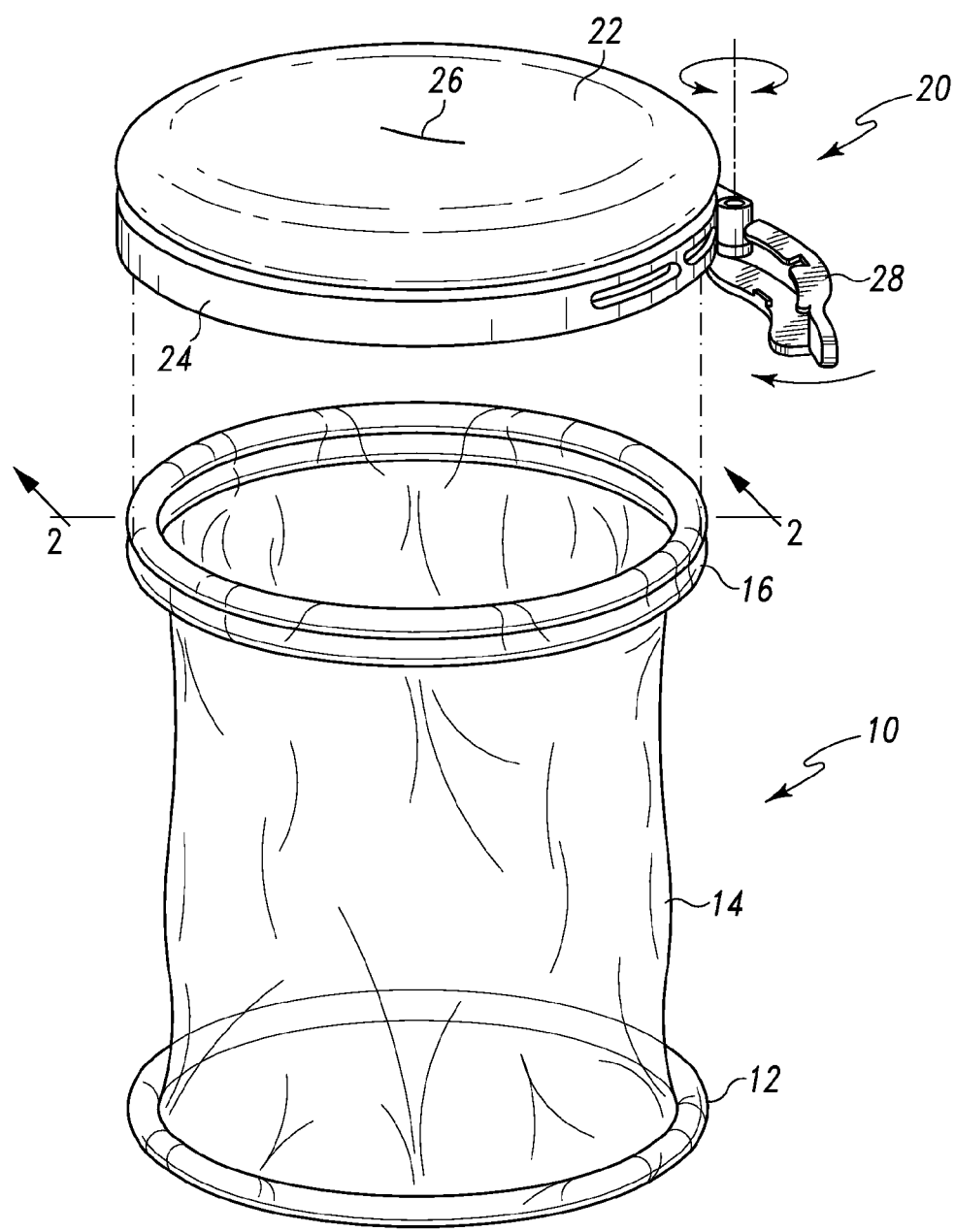
FIG. 1 depicts an exploded perspective view of an access port and a wound protector.

FIG. 1 illustrates an example of a surgical access device. The device includes a wound protection (10) and a hand access port (20). The wound protector (10) in this example is a flexible variable length roll-up type of wound protector. Naturally, other types of wound protectors may also be used, including without limitation flexible fixed length wound protectors, flexible variable length pull-up types of wound protectors, rigid wound protectors, and the like. In this embodiment the distal ring (12) is circular ring with a circular cross-sectional geometry; however, non-circular rings and non-circular cross-sectional geometries are also possible. For instance, the distal ring could have an oval or elliptical in cross-sectional shape. In this embodiment the sleeve (14) is a single layered tube of material; however, a discontinuous sleeve or multi-layered sleeves are also possible. The sleeve (14) may be transparent, translucent, or opaque. As shown here, the sleeve (14) is fastened at its ends to the proximal and distal rings (12, 16) using an adhesive or heat sealing techniques; however, alternative techniques may also be employed. The length of the sleeve (14) can also vary. For instance, the sleeve may be between 2 cm and 14 cm in length; however, other lengths are also possible. The thickness of the sleeve (14) can also vary.

In this embodiment the proximal ring (16) is a circular ring; however, non-circular rings are also possible. The proximal ring (16) can also vary in size, but is preferably sized to receive a surgeon's hand. Optionally, the ratio of the distal ring (12) and proximal ring (16) diameters is between 0.4 and 1.2. The proximal ring (16) can take a variety of different cross-sectional geometries. In this embodiment, the proximal ring (16) is formed from an extruded polymer with a cross-sectional geometry of has a generally figure eight shape. The extruded material is shaped into a ring with metal wires inserted in the two annuli. Naturally, other geometries are also contemplated.

Figure 2:
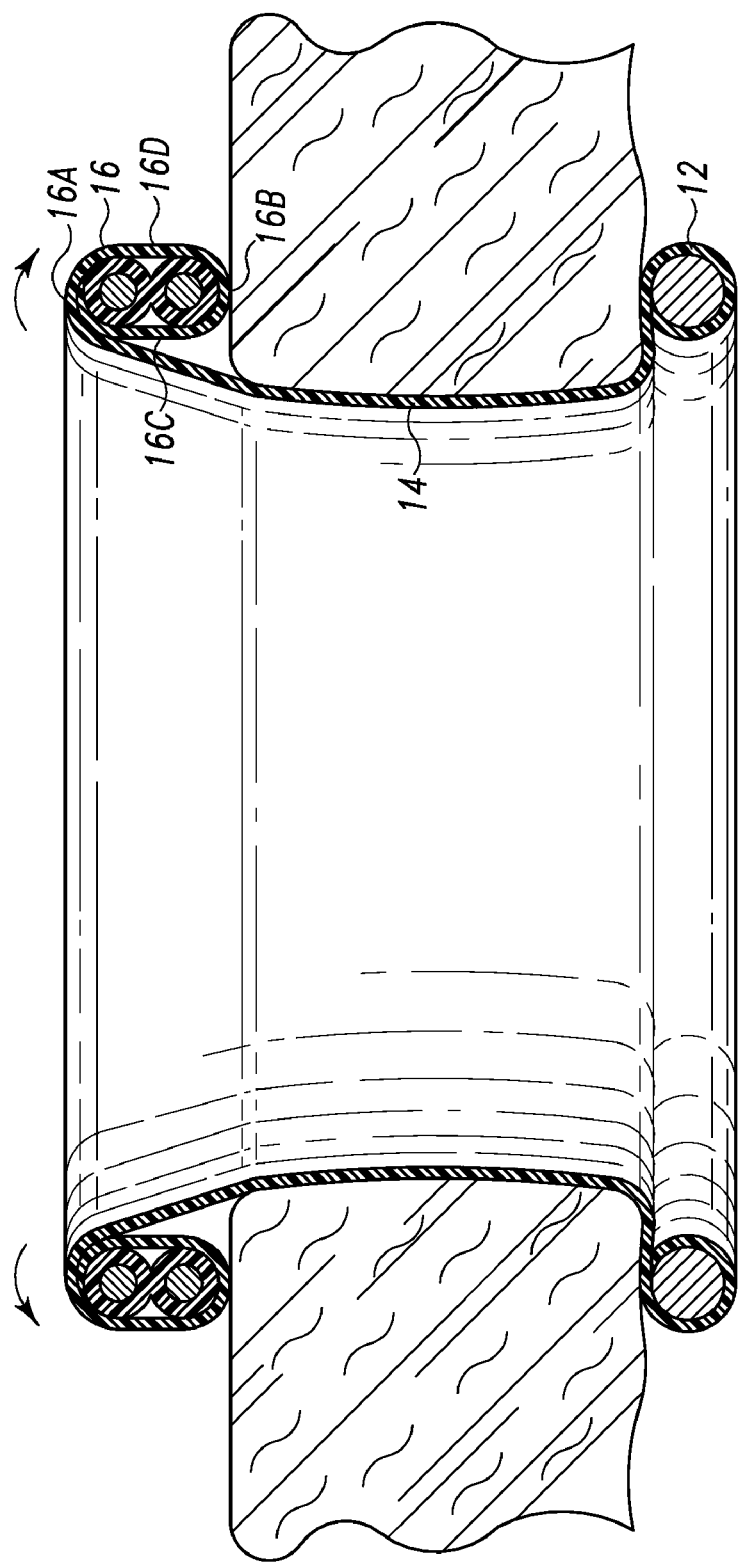
FIG. 2 depicts a cross-sectional view of a deployed wound protector.

FIG. 2 depicts an example of the wound protector (10) in a deployed position in a patient. In this example the wound protector in positioned in a patient's abdominal wall through an incision. To deploy the wound protector, the distal ring (12) is held in a collapsed position (e.g., in an oblong shape like an oval, a peanut, a figure eight, and the like) to reduce its size and then inserted through the incision. After insertion, the distal ring (12) is released and then expands to its ring-like shape. As shown here, the expanded distal ring (12) is larger than the incision and sits against the peritoneal surface of the abdominal wall.

The proximal ring (16) includes a proximal face (16A), a distal face (16B), a medial face (16C), and a lateral face (16D). The proximal ring (16) is rollable to gather the flexible sleeve (14) around the proximal ring (16), and the distal face (16B) sits on the cutaneous surface of the abdominal wall (40). In the deployed position the proximal and distal rings (12, 16) are substantially aligned axially. The proximal ring (16) is rollable in the outward directions (as shown by the arrows) to shorten the sleeve (14) and in the inward direction to lengthen the sleeve (14), or vice versa. For the purposes of illustration, the sleeve (14) is depicted with an exaggerate thickness. Ordinarily in the deployed state the sleeve (14) would be wound many times around the proximal ring. The shortening of the sleeve (14) pulls the sleeve (14) taut against the incised wound defining an access passage. As one with ordinary skill in the art will recognize, surgical procedures can be performed through the incision and the sleeve (14) protects the incised wound from infection and contamination. In addition, the taut sleeve (14) tends to pull the incised wound open thus functioning as a wound retractor. As demonstrated in this example, more retraction is possible by rolling the proximal ring (16) outward, while less retraction is possible by rolling the proximal ring (16) inward.

The hand access port (20) in this example comprises a resilient pad (22) circumscribed by a rigid frame (24). The pad (22) has a central aperture (26). In use the aperture (26) will stretch open to receive and seal against a surgeon's arm. A surgeon's hand will typically be lubricated to facilitate ingress and egress. The aperture (26) can take a variety of different shapes and forms, but in the present example comprise an axial slit. The aperture (26) in this example is self-closing in the absence of a surgeon's arm. The latch (28) allows the hand access port (20) to be selectively attachable and detachable from the proximal ring (16) of the wound protector (10). Naturally, a wide variety of other attaching mechanisms could also be used. It is contemplated that the access port (20) and wound protector (10) could be integrally connected and not detachable.

Figure 3:
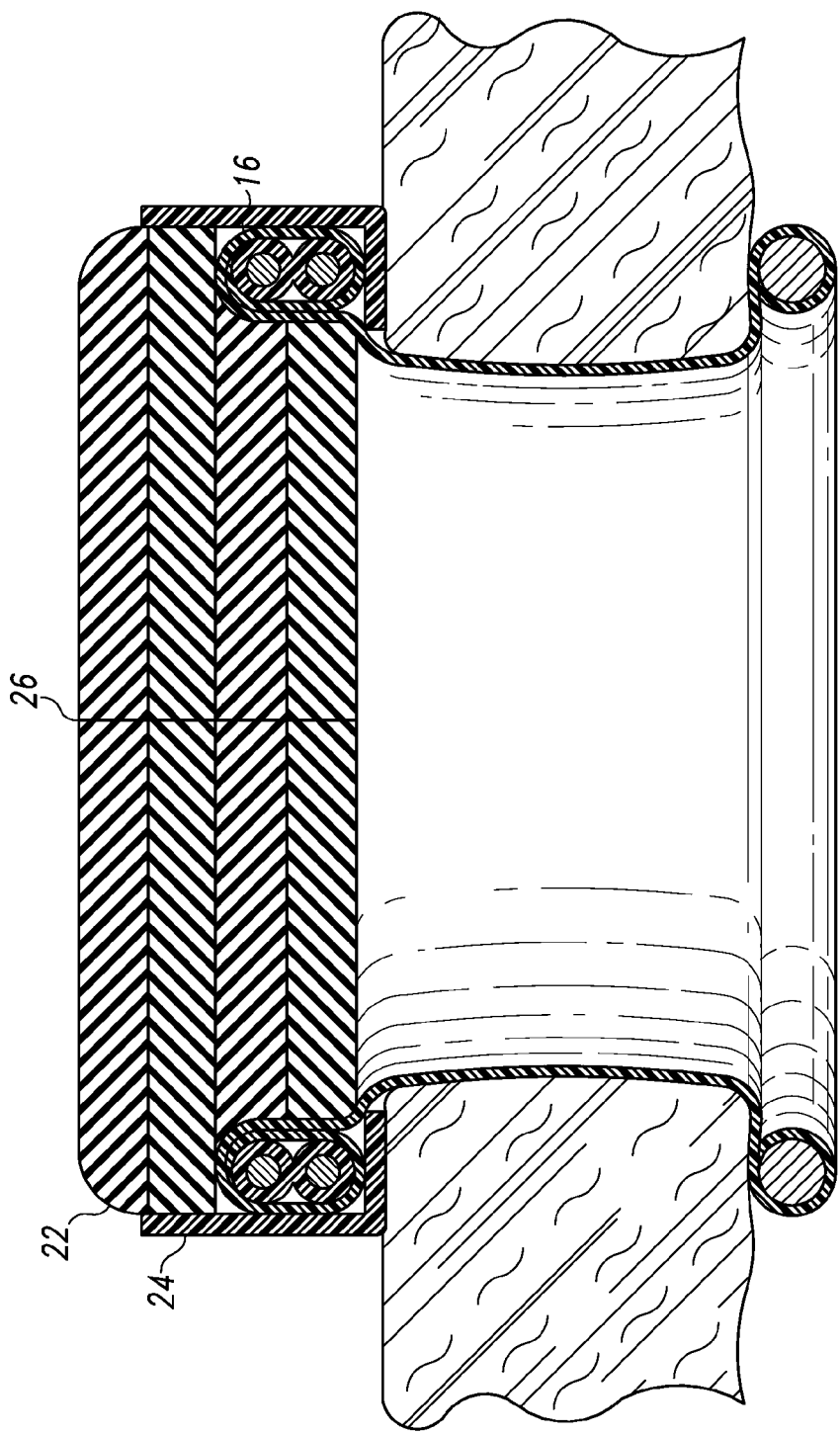
FIG. 3 depicts a cross-sectional view of a deployed wound protector and composite access port.

FIG. 3 illustrates a cross-sectional view of the hand access port (20) attached to a wound protector (10). The resilient quality of the pad (22) seals against the proximal ring (16). The pad (22) in this example is a composite structure formed from a plurality of laminated layers. The composite structure may be varied to achieve desired performance characteristics of the hand access port (20), including one or more other following non-limiting examples: providing good sealing against surgeon's arm, reducing constricting force induced by the pad (22) on a surgeon's arm positioned in the aperture, reducing the pad (22) thickness, preventing pad (22) "tenting" or "ballooning" induced the pneumoperitoneum, increasing the pad (22) toughness to prevent ripping or puncture, and the like. The layers may be the same thickness, as shown in this example, or may have varying thicknesses. The layers may be permanently attached to one another or may be delaminated if desired. The composite structure may have substantially co-extensive planer layers, as shown in this example as discs, or may have discrete non-planer composite structures.

The various composite parts in the pad (22) may be formed from the same or disparate materials. A wide range of different materials may be used. For instance, one or more layers could be formed from an open-cell or closed cell foam made with neoprene, polyethylene, or the like. In an alternative embodiment, the pad can be made from a gel material. Gel materials are known in the art have typically have a low durometer, high elongation, and good tear strength. In one example, a gel material may have an ultimate elongation less than about 1000 percent and a durometer not less than about 5 Shore A. In another example, the gel material may have an ultimate elongation greater than about 1000 percent and a durometer less than about 5 Shore A, which is sometimes referred to as an "ultragel."

Figure 4:
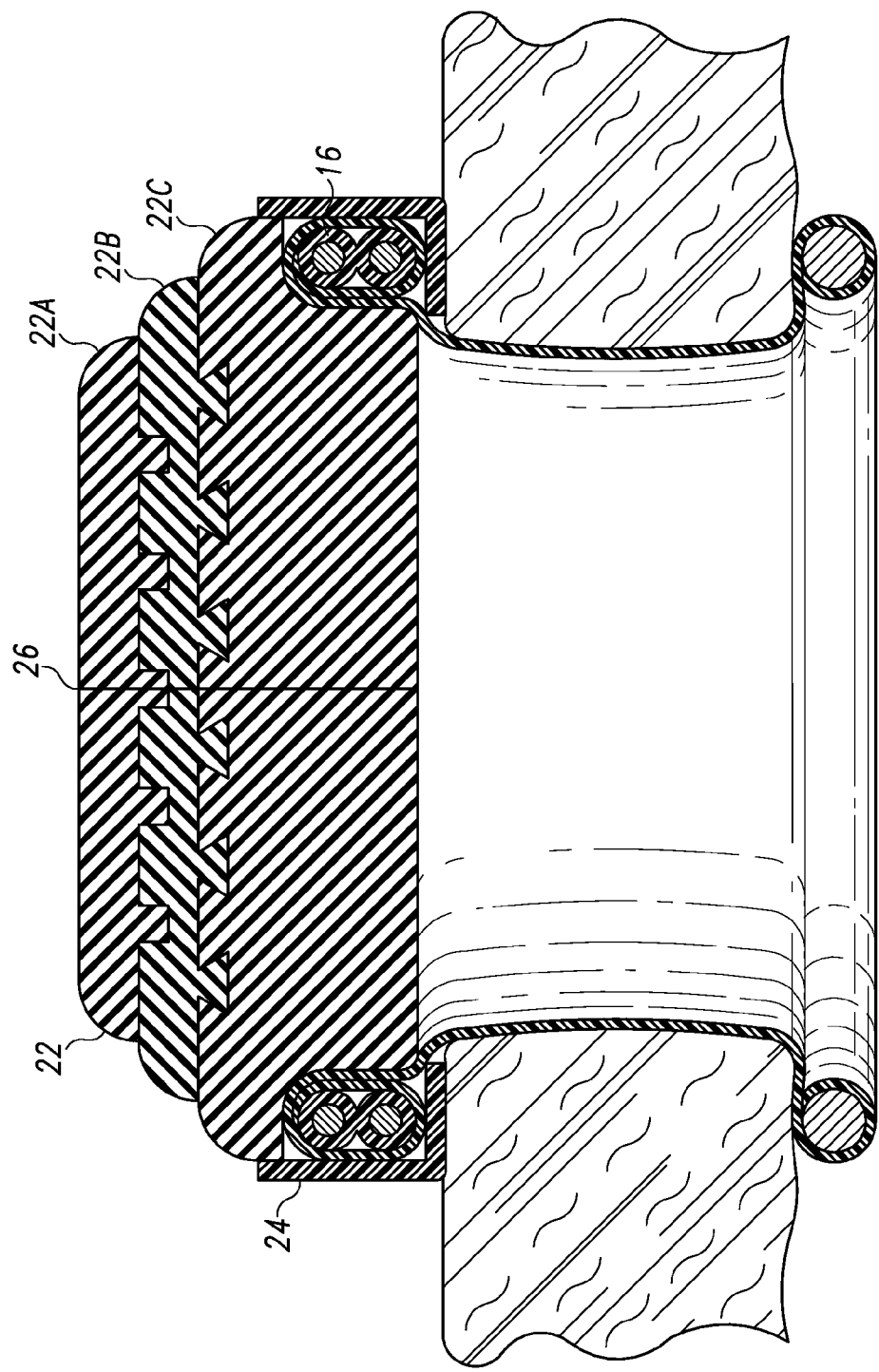
FIG. 4 depicts a cross-sectional view of a deployed wound protector and composite access port.

FIG. 4 illustrates another embodiment where the composite layered portions the pad (22) layers are partially co-planer. The layers in this example are attached to one another by a mechanical friction fit and may be augmented by an adhesive. The layers (22A, 22B) are interconnected with a square stepped tenon and mortise features. The layers (22B, 22C) are interconnected with dovetail tenon and mortise features. In this example one or both layers (22A, 22B) may be selectively removed from the pad (22) to change the performance characteristics of the of the hand access port (20) during surgery.

Figure 5:
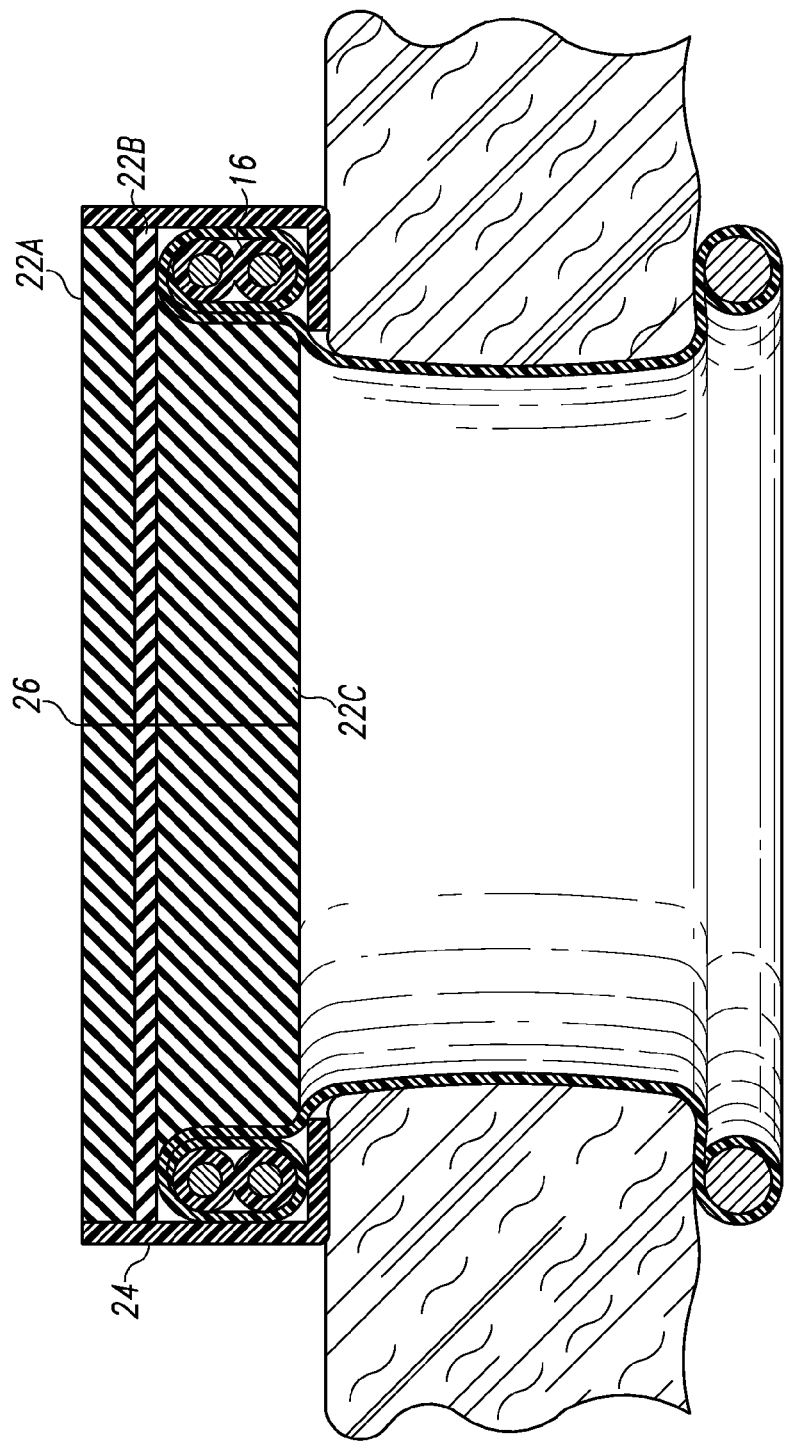
FIG. 5 depicts a cross-sectional view of a deployed wound protector and composite access port.

FIG. 5 illustrates another embodiment where the composite portions the pad (22) are substantially co-extensive planer layers have varying thicknesses. The layers in this example are attached to one another by a using a curing process or adhesives. The layers (22A, 22C) are made from a gel material, while the layer (22B) is comparatively thinner and is a resilient diaphragm made from silicone, polyisoprene, polyurethane, or the like. Note that the layer (22B) may include an enlarged aperture compared to the aperture (26) slits in layers (22A, 22C). In another variation, the pad (22) may include only layers (22A, 22B) or layers (22B, 22C).

Figure 6:
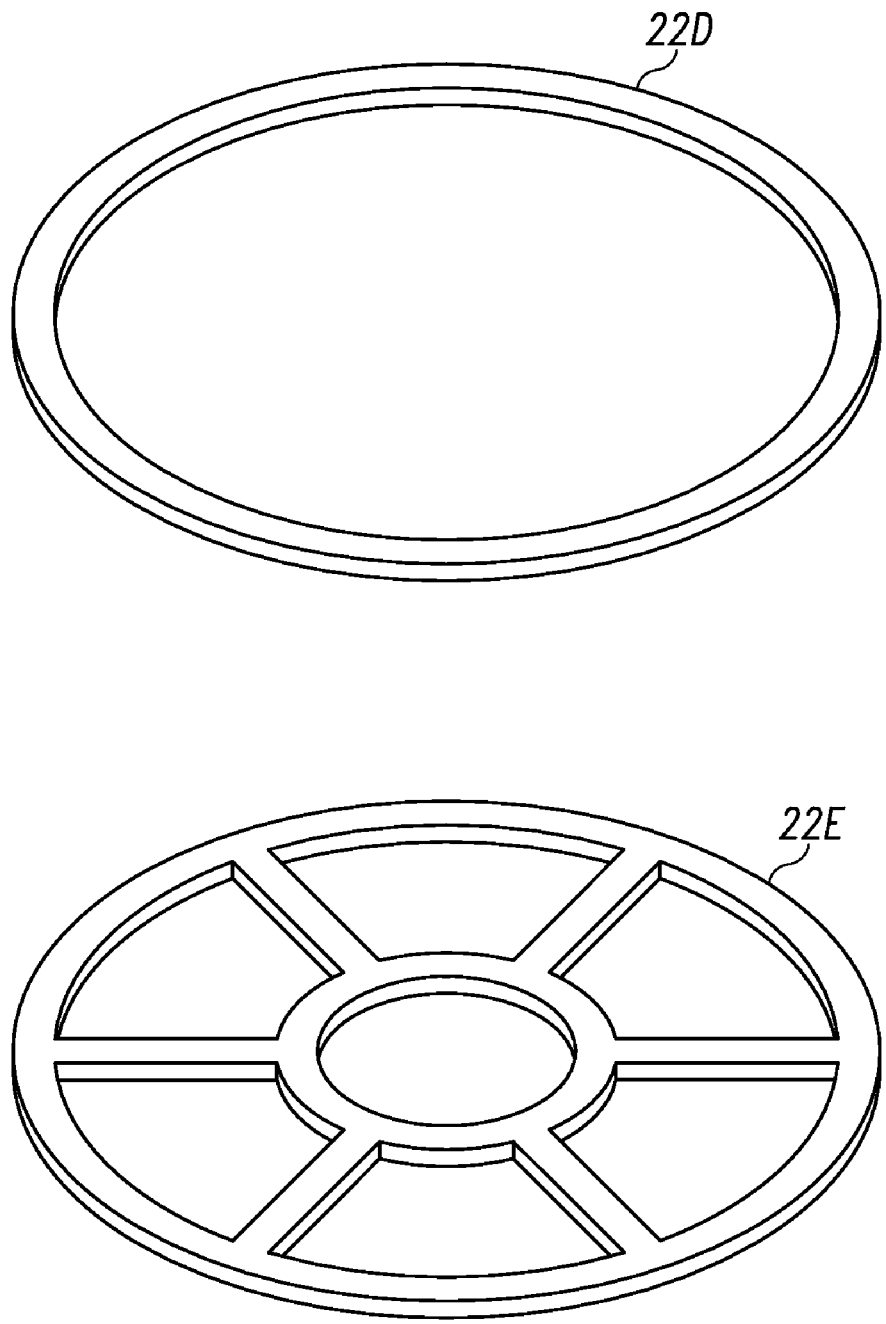
FIG. 6 depicts examples of composite reinforcing structures.

FIG. 6 illustrates two variations of the prior example to substitute the intermediate composite portion (22B) with a composite stature that is not a co-extensive planer layer. In these variations the composite portion is a reinforcing structure encapsulated in the pad (22), where layers (22A, 22C) are homogenous or heterogeneous. The composite portion may be made from silicone, polyisoprene, polyurethane, or the like, but other materials may also be used. The first variation is a flat o-ring (22D) that would be positioned co-axially with the aperture (26). The 0-ring structure is effective at increasing hoop-stress about the aperture (26). The second variation has a composite portion (22E) comprising two flat o-rings connected by radial ribs. The 0-ring structure is effective for increasing hoop-stress about the aperture (26), while the ribs are effective at preventing tenting.

Preferably, the devices described above will be processed before surgery. First, a new or used device is obtained and if necessary cleaned. The device can then be sterilized. In one sterilization technique the access device is placed in a closed and sealed container, such as a plastic or TYVEK bag. Optionally, the device can be bundled in the container as a kit with other components, including one or more of the following: a wound protector, hand access port, a mounting ring for the wound protector, a tube of lubricant, a marker, an incision template or scale, an instruction sheet, and the like. The container and device, as well as any other components, are then placed in a field of radiation that can penetrate the container, such as gamma radiation, x-rays, or high-energy electrons. The radiation kills bacteria on the device and in the container. The sterilized device can then be stored in the sterile container. The sealed container keeps the device sterile until it is opened in the medical facility.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. In addition, the foregoing teachings could be implemented for non-HALS procedures, such as reducing the scale to seal against instruments in traditional laparoscopic procedures. Accordingly, the scope of the present invention should be considered in terms of the following claims and is understood not to be limited to the details of structure, materials, or acts shown and described in the specification and drawings.

The invention claimed is:

1. A surgical access port, comprising:
   a) a resilient gel pad attached comprising an aperture adapted to receive and seal against a surgeon's arm or surgical instruments, the aperture being self-closing in the absence of a surgeon's arm or surgical instrument;
   b) a first resilient o-ring encapsulated in the gel pad, the first o-ring circumscribing the aperture;
   c) a second resilient o-ring encapsulated in the gel pad, the second o-ring circumscribing the first resilient o-ring; and
   d) a wound protector.

2. The surgical access port of claim 1, further comprising a plurality of resilient ribs extending radially between the first and second o-rings.

3. A method of processing a device for surgery, comprising:
 a) obtaining the surgical access port of claim 1;
 b) sterilizing the surgical access port; and
 c) storing the hand surgical port in a sterile container.

4. A surgical device, comprising:
 a) a hand access port comprising:
  (i) a resilient pad attached comprising an aperture adapted to receive and seal against a surgeon's arm or surgical instruments, the aperture being self-closing in the absence of a surgeon's arm or surgical instrument;
  (ii) a first resilient o-ring encapsulated in the pad, the first o-ring circumscribing the aperture;
  (iii) a second resilient o-ring encapsulated in the pad, the second o-ring circumscribing the first resilient o-ring; and
 b) a wound protector connected to the hand access port.

5. A surgical device, comprising:
 a) a hand access port comprising:
  (i) a resilient pad attached comprising an aperture adapted to receive and seal against a surgeon's arm or surgical instruments, the aperture being self-closing in the absence of a surgeon's arm or surgical instrument;
  (ii) a first resilient o-ring encapsulated in the pad, the first o-ring circumscribing the aperture;
  (iii) a second resilient o-ring encapsulated in the pad, the second o-ring circumscribing the first resilient o-ring;
  (iv) a plurality of resilient ribs extending radially between the first and second o-rings; and
 b) a wound protector connected to the hand access port.

\* \* \* \* \*